US00PP25386P3

(12) United States Plant Patent
Brazelton et al.

(10) Patent No.: US PP25,386 P3
(45) Date of Patent: Mar. 31, 2015

(54) BLUEBERRY PLANT NAMED 'LAST CALL'

(50) Latin Name: ***Vaccinium corymbosum* hybrid**
Varietal Denomination: Last Call

(71) Applicant: Fall Creek Farm and Nursery, Inc., Lowell, OR (US)

(72) Inventors: David M. Brazelton, Walterville, OR (US); Adam L. Wagner, Eugene, OR (US)

(73) Assignee: Fall Creek Farm and Nursery, Inc., Lowell, OR (US)

( * ) Notice: Subject to any disclaimer, the term of this patent is extended or adjusted under 35 U.S.C. 154(b) by 0 days.

(21) Appl. No.: 13/694,909

(22) Filed: Jan. 18, 2013

(65) Prior Publication Data

US 2014/0208465 P1 Jul. 24, 2014

(51) Int. Cl.
*A01H 5/00* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

PP10,035 P 9/1997 Moore

*Primary Examiner* — Anne Grunberg
(74) *Attorney, Agent, or Firm* — Davis Wright Tremaine LLP

(57) ABSTRACT

The new blueberry plant variety 'Last Call' is provided. 'Last Call' is a commercial variety intended for both the fresh and process markets. The variety produces a large, light blue berry with exceptional flavor and firmness. 'Last Call' fruit ripens at the same time as the latest season commercial cultivars 'Elliott' and 'Aurora' but has a sweeter flavor that was preferred in blind taste tests. The variety has a vigorous bush that had higher yields than 'Aurora' in 2011-2012 in Oregon (yields were observed but not measured in 2010). The fruit of 'Last Call' had better firmness than 'Elliott' before and after storage (measured with a Firmtech 2 fruit firmness tester). 'Last Call' is a vigorous plant with an upright growth habit, and an estimated chilling requirement of 1000 hours based on pedigree.

3 Drawing Sheets

Latin name of the family, genus, and species:
Family—Ericaceae.
Genus—*Vaccinium.*
Species—*corymbosum* hybrid.
Variety denomination: The new blueberry plant claimed is of the variety denominated 'Last Call'.

CROSS REFERENCE TO RELATED APPLICATIONS

None.

STATEMENT REGARDING FEDERALLY-SPONSORED RESEARCH AND DEVELOPMENT

None.

BACKGROUND OF THE INVENTION

The present invention relates to the discovery of a new and distinct cultivar of northern highbush hybrid blueberry (*Vaccinium corymbosum* hybrid) and referred to as 'Last Call', as herein described and illustrated.

The new blueberry plant variety 'Last Call' was selected in Lowell, Oreg. in 2006. 'Last Call' is a commercial variety intended for both the fresh and process markets. The variety produces a large, light blue berry with exceptional flavor and firmness. 'Last Call' fruit ripens at the same time as the latest season commercial cultivars 'Elliott' and 'Aurora' but has a sweeter flavor that was preferred in blind taste tests. The variety has a vigorous bush that had higher yields than 'Aurora' in 2011-2012 in Oregon (yields were observed but not measured in 2010). The fruit of 'Last Call' had better firmness than 'Elliott' before and after storage (measured with a Firmtech 2 fruit firmness tester). 'Last Call' is a vigorous plant with an upright growth habit, and an estimated chilling requirement of 1000 hours based on pedigree.

Pedigree and History: The new blueberry plant originated from a 2002 controlled cross pollination of 'Ozarkblue' (pollen parent, U.S. Plant Pat. No. 10,035) by 'Elliott' (female parent, unpatented). The seedling was first selected from a high density field planting in the summer of 2006. 'Last Call' was propagated using traditional techniques and has been planted in replicated trials since 2008, alongside standard commercial varieties. Fruit quality and yields have been observed in a plot of 9 plants in the years 2010, 2011, and 2012. In comparison to the parent variety 'Ozarkblue', 'Last Call' differs from pollen parent 'Ozarkblue' in that 'Last Call' ripens about 2 weeks later (in Lowell, Oreg.), and has firmer fruit that is more flattened (oblate) and has a wider calyx end depression.

'Last Call' was selected because it was late maturing, firm, and flavorful. Late season fruit commands a premium price in the market because of limited availability, but the current very late season cultivars 'Elliott' and 'Aurora' tend to produce tart fruit. In addition, 'Elliot' fruit often gets soft and wrinkly, whereas 'Aurora' plants are small in stature and tend to yield poorly during orchard establishment.

The new variety can be compared to female parent 'Elliott' in that 'Last Call' has larger berries with better firmness and sweeter flavor. In comparison to female parent 'Elliott', 'Last Call' has firmer, larger fruit that is more flavorful. 'Last Call' fruit is also more flattened (oblate) with a larger calyx end depression than 'Elliott'.

The new variety can be compared to the commercial variety 'Aurora' in that 'Last Call' has a more vigorous plant with better yields on 3 and 4 year old plants, and berries with sweeter flavor.

The new blueberry plant variety 'Last Call' has maintained its distinguishing characteristics throughout successive asexual propagations. The variety has been repeatedly asexually reproduced through softwood cuttings in Lowell, Oreg., and the clones are phenotypically identical to the original plant.

SUMMARY OF THE INVENTION

The new blueberry plant variety 'Last Call' has not been observed under all possible environmental conditions. The phenotype may vary somewhat with variations in environment and cultural practices such as temperature and light intensity without, however, any variance in genotype.

The following traits have been repeatedly observed in Lowell, Oreg., and are determined to be the unique characteristics of the new blueberry plant variety 'Last Call':

1. Late season ripening
2. High yields
3. Large, flavorful, firm fruit

BRIEF DESCRIPTION OF THE DRAWINGS

The accompanying photographic illustration shows typical specimens in full color of the foliage and fruit of the new variety 'Last Call'. The colors are as nearly true as is reasonably possible in a color representation of this type.

BOTANICAL DESCRIPTION

Figure 1:
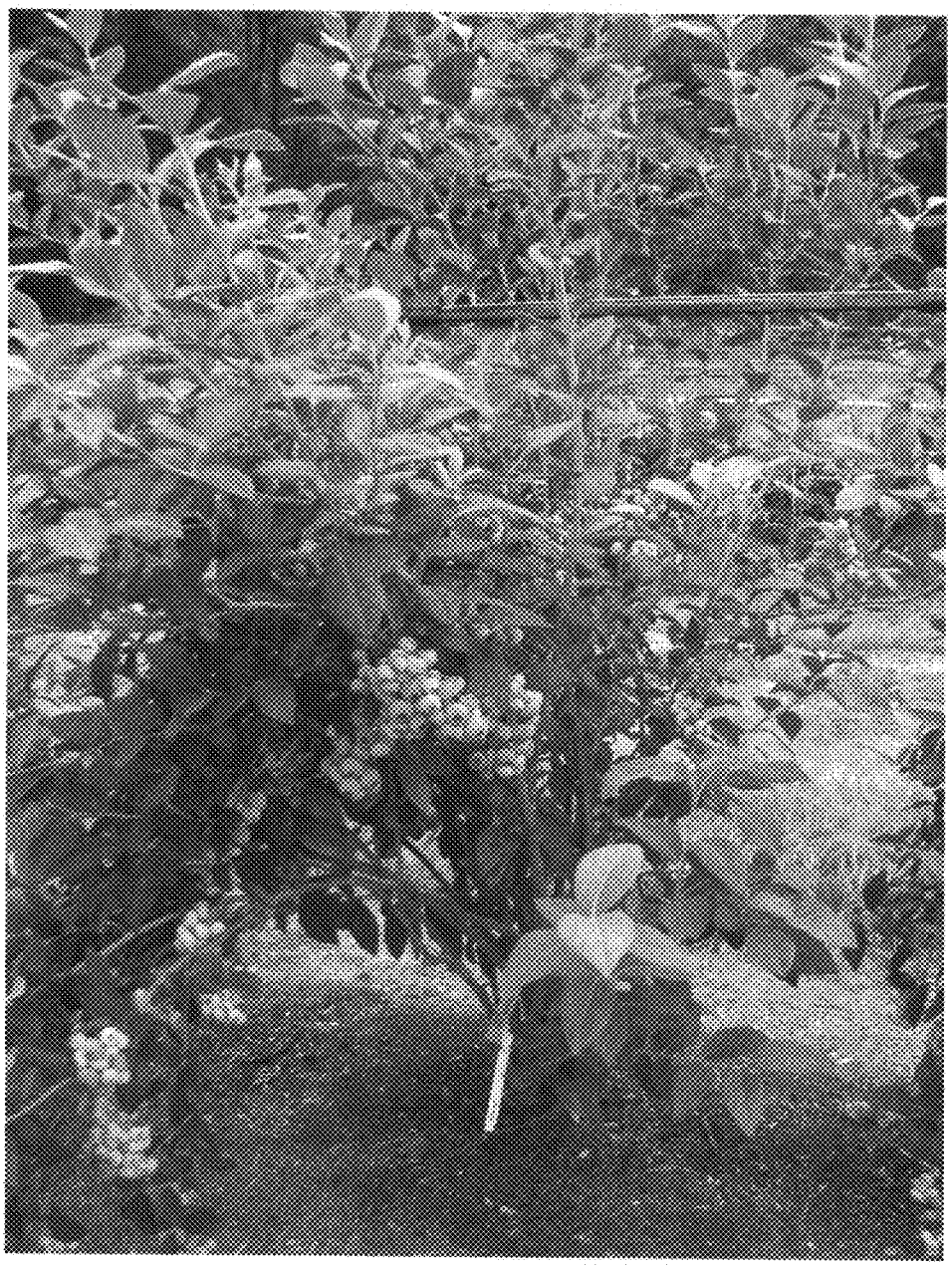
FIG. 1 is a photograph of the new variety 'Last Call'.
Figure 2:
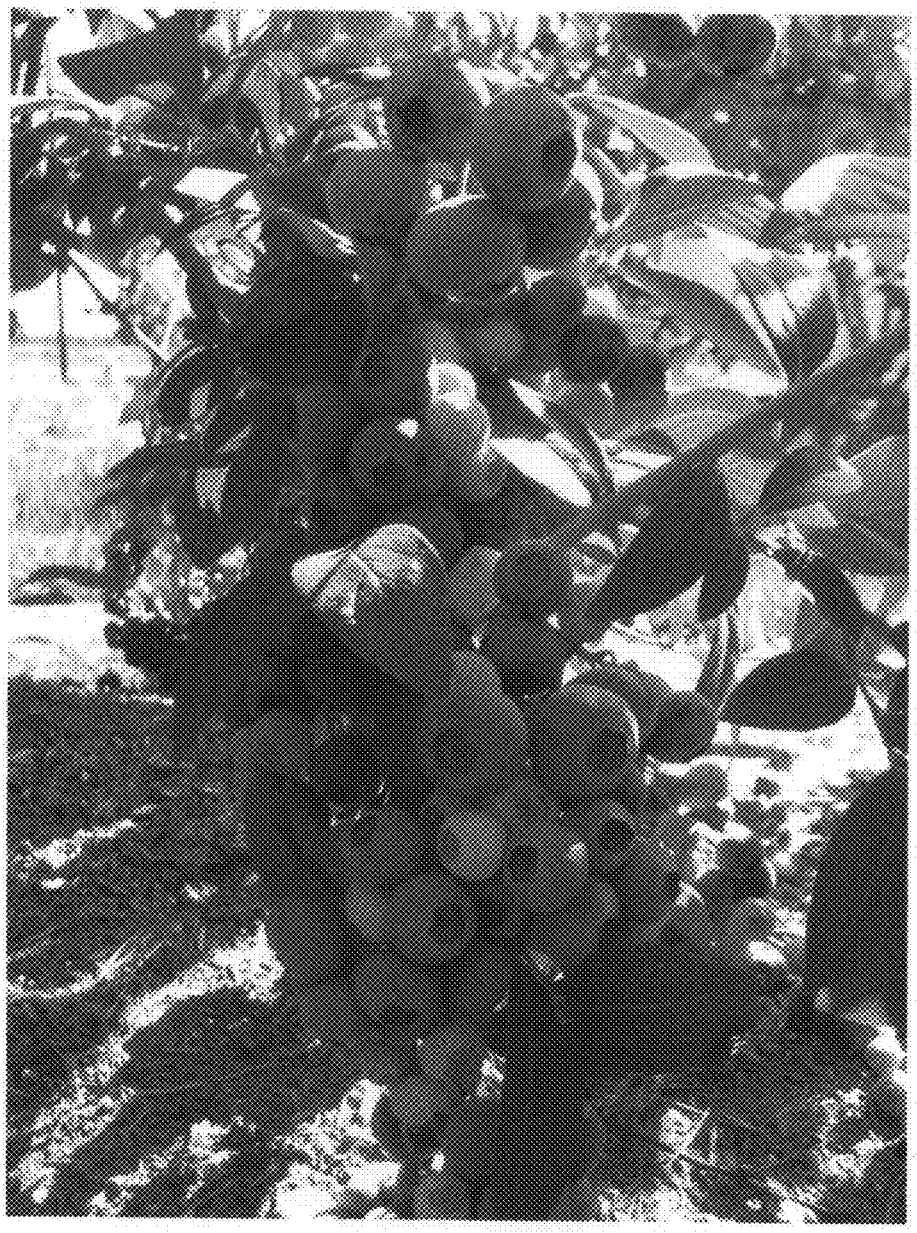
FIG. 2 is a photograph of the fruit of the new variety 'Last Call'.
Figure 3:
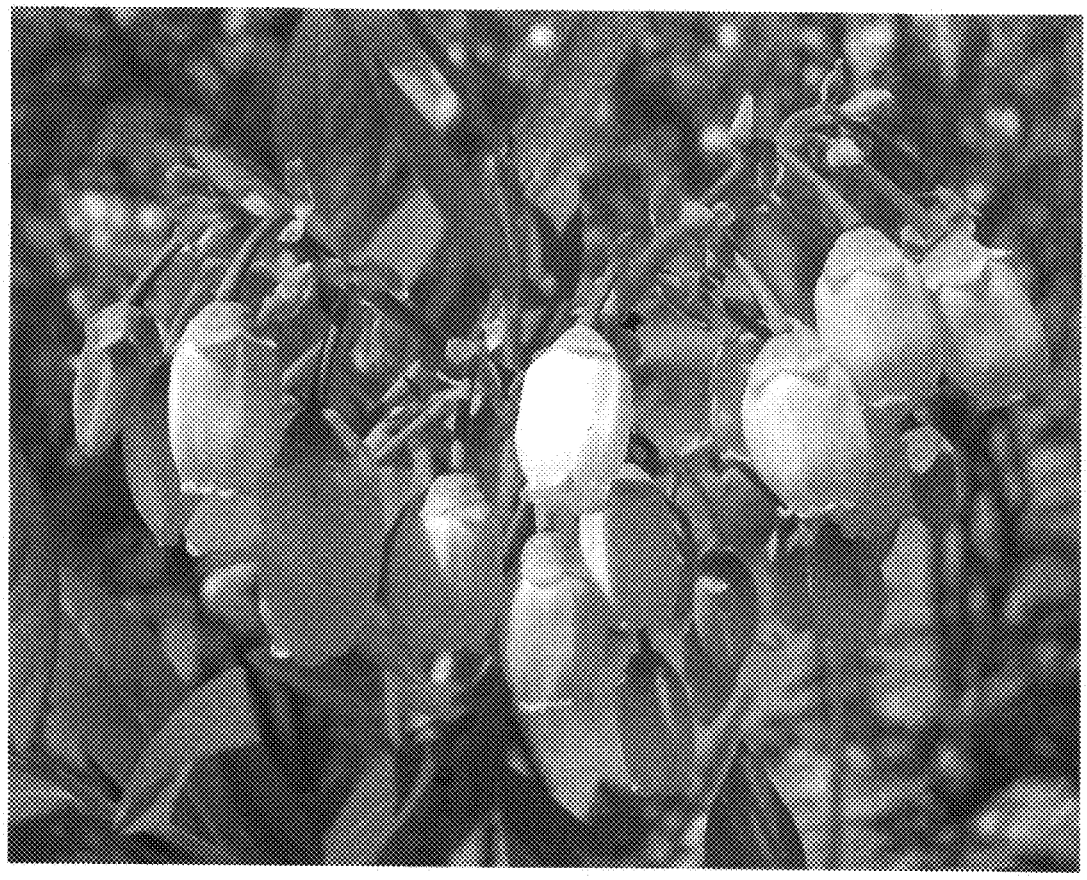
FIG. 3 is a photograph of the flowers of the new variety 'Last Call'.

The following detailed description sets forth the distinctive characteristics of 'Last Call'. The data which defines these characteristics was collected from asexual reproductions of the original selection. Dimensions, sizes, colors and other characteristics are approximations and averages set forth as accurately as possible. The plant history was taken on plants that were three and four years old, and the descriptions relate to plants grown in the field in Lowell, Oreg. Color designations are from "The Pantone Book of Color" (by Leatrice Eiseman and Lawrence Herbert; Harry N. Abrams, Inc., Publishers, New York, 1990). Where the Pantone color designations differ from the colors in the photographs, the Pantone colors are accurate.

Classification:

*a. Family*.—Ericaceae.
*b. Genus.—Vaccinium.*
*c. Species.—corymbosum* hybrid.
*d. Common name*.—Northern Highbush hybrid.

Parentage: Female Parent — 'Elliott' (unpatented). Male parent — 'Ozarkblue' (U.S. Plant Pat. No. 10,035).

Market class: 'Last Call' is a commercial blueberry variety intended for both fresh and process markets.

PLANT

Height of plant: 4 year old plants average 48" in height.

Canopy diameter: 4 year old plants average 30" in diameter.

Growth habit: Upright.

Plant vigor: Vigorous.

Twigginess: Low.

Suckering: Low.

Evergreenness: Deciduous.

Chilling requirement: Estimated at 1000 hours, based on pedigree.

Cold hardiness: Estimated to be USDA zones 7-8, based on pedigree.

Productivity in Lowell, Oreg:

*a.* 3 *year old plants*.—'Last Call' yielded 6.39 lbs per plant, compared to 7.61 bs per plant on 'Elliott' and 3.83 lbs per plant on 'Aurora'.
*b.* 4 *year old plants*.—'Last Call' yielded 9.6 lbs per plant, compared to 9.7 lbs per plant on 'Elliott' and 5.71 lbs per plant on 'Aurora'.

Propagation: Hardwood propagation of 'Last Call' has been successful, softwood propagation has been moderately successful.

Disease resistance/susceptibility:

*a. Root rot* (*Phytophthora cinnamomi*).—Does not appear to be overly susceptible.
*b. Stem blight* (*Botryosphaeria spp*).—Undetermined.
*c. Phomopsis twig blight* (*Phomopsis vaccinii*).—Does not appear to be overly susceptible.
*d. Botryosphaeria stem canker* (*Botryosphaeria corticis*).—Undetermined.
*e. Bacterial cane canker* (*Pseudomonas syringae*).—Does not appear to be overly susceptible.
*f. Botrytis blight* (*Botrytis cinerea*).—Does not appear to be overly susceptible.
*g. Leaf spot* (*Septoria spp.*).—Does not appear to be overly susceptible.
*h. Leaf rust* (*Naohidemyces vaccinii*).—Does not appear to be overly susceptible.
*i. Bud mites* (*Acalatus vaccinii*).—Undetermined.

Survival: Good.

TRUNK AND BRANCHES

Texture:

*a. Surface texture new wood*.—Smooth.
*b. Surface texture* 1 *year wood*.—Smooth.
*c. Surface texture* 3 *year wood*.—Rough.

Color:

*a. Color new wood*.—Pantone color Green Oasis 15-0538.
*b. Color bark* 1 *year*.—Pantone color Green Oasis 15-0538 and Maroon 18-1619.
*c. Color rough bark* 3 *year*.—Pantone color Brush 16-1317, Gray Sand 13-1010 and Maroon 18-1619.

FOLIAGE

Internode length: Average of 22.1 mm.
Leaf dimensions:
- *a. Leaf length*.—Average of 75.32 mm, including petiole.
- *b. Leaf width*.—Average of 36.6 mm.

Leaf shape: Broadly elliptic.
Leaf margin: Entire.
Leaf color:
- *a. Upper leaf surface*.—Pantone color Black Forest 19-0315.
- *b. Lower leaf surface*.—Pantone color Hedge green 17-6323.
- *c. Fall foliage color*.—Pantone colors Holly Berry 17-1633, Maroon 18-1619, Chrysanthemum 17-1641, Claret Red 17-1740, Lemon Drop 12-0736, Banana 13-0947, and Black Forest 19-0315.

Pubescence:
- *a. Upper leaf surface*.—Absent.
- *b. Lower leaf surface*.—Absent.
- *c. Leaf margins*.—Absent.

Petiole:
- *a. Length*.—Average 2.84 mm.
- *b. Color*.—Pantone color Mellow Green 12-0426.
- *c. Surface texture*.—Smooth.

Leafing vs flowering: In Lowell, Oreg. flower bud break occurs prior to vegetative bud break. Flowers persist during initial vegetative growth period.

FLOWERS

Flower arrangement: Flowers are arranged alternately along a short, leafless branch.
Immature flower color: Pantone color Rapture Rose 17-1929 and Pastel Parchment 11-0603.
Fragrance: Sweet.
Pedicel:
- *a. Pedicel length flower*.—Variable length, average at terminal end 8.1 mm.
- *b. Pedicel color*.—Pantone color Green Olive 17-0535.

Peduncle:
- *a. Peduncle length flower*.—Variable length, average 32.0 mm.
- *b. Peduncle color*.—Pantone color Apple Green 15-0543.

Anther:
- *a. Anther length*.—Average 3.96 mm.
- *b. Anther color*.—Pantone color Golden Ochre 16-1346 and Hazel 17-1143.

Flower shape: Cylindrical to urceolate.
Pollen:
- *a. Pollen staining*.—95% viable, Staining with 2% acetocarmine.
- *b. Pollen abundance*.—Moderate.
- *c. Pollen color*.—Pantone color Corn Husk 12-0714.

Flower length: Average of 11.02 mm.
Corolla:
- *a. Corolla length*.—Average of 8.53 mm.
- *b. Corolla diameter*.—Average of 7.5 mm.
- *c. Corolla color*.—Pantone color Pastel Parchment 11-0603.
- *d. Corolla texture*.—Smooth.
- *e. Corolla aperture*.—Average of 5.21 mm.

Style length: Average of 8.22 mm.
Calyx:
- *a. Calyx diameter*.—Average of 5.41 mm.
- *b. Calyx surface*.—Smooth.
- *c. Calyx color*.—Pantone color Peridot 17-0336 and Tarragon 15-0326.

Pistil color: Pantone color Apple Green 15-0543.
Flowering period: Late April through mid-May in Lowell, Oreg.
Flowering cluster: Loose cluster with long pedicels and peduncles.
Number of flowers: Average 13 flowers per cluster.
Stigma location: Stigma location varies from an average of 0.13 mm above the lip of corolla to an average of 0.18 mm below the lip of corolla.
Self-compatibility: Moderate. On crosses done in a field plot, 54% of self-pollinated flowers reached maturity, compared to 61% of flowers crossed with commercial variety Draper.

FRUIT

Mean harvest date: August 17.
Mean date last pick: September 25.
Calyx:
- *a. Calyx aperture*.—Average 6.42 mm.
- *b. Calyx lobes*.—Indistinct.
- *c. Calyx depth*.—Average 2.36 mm.

Berry cluster: Loose.
Berries per cluster: Average 10-12.
Berry pedicel length: Average 14.59 mm.
Pedicel surface texture: Smooth.
Berry peduncle:
- *a. Length*.—Average 49.37 mm.
- *b. Peduncle surface texture*.—Smooth.

Berry detachment: Easy.
Berry weight: Average 2.15 g per berry, compared to 'Elliott' plants of the same age 1.72 g per berry, and compared to 'Aurora' plants of the same age 1.93 g per berry.
Berry height: Average 12.86 mm.
Berry width: Average 18.44 mm.
Berry shape: Oblate.
Berry skin color on plant: Pantone color Dapple Gray 16-3907.
Berry skin color after harvest: Pantone color Dapple Gray 16-3907 to Night Shadow Blue 19-3919.
Berry skin color after polishing: Pantone color Dark Navy 19-4013.
Berry wax: Moderate wax and moderately persistent.
Berry flesh color: Pantone color Nude 12-0911 to Autumn Blonde 12-0813.
Pedicel scar: Small and dry, average diameter 1.28 mm.
Berry firmness: Good. Average berry firmness measurement 196.07 g/mm of deflection compared to 'Elliott' berries harvested on the same day that measured 176.81 g/mm of deflection as measured by a Firmtech fruit firmness tester.
Berry flavor: Similar to early blueberry cultivars such as 'Earliblue' or 'Jersey', less acidic than 'Elliott' or 'Aurora'.
Berry texture: Smooth.

SEEDS

Seed color: Pantone color Henna 19-1334.
Seed length: Average 1.97 mm.
Seed width: Average 1.23 mm.
Seed weight: Average 0.55 mg.
Quantity seeds per berry: Average 44 seeds per berry.

It is claimed:

1. A new and distinct variety of blueberry plant named 'Last Call', substantially as illustrated and described herein.

* * * * *